United States Patent [19]

Eichel et al.

[11] Patent Number: 5,529,790

[45] Date of Patent: *Jun. 25, 1996

[54] DELAYED, SUSTAINED-RELEASE DILTIAZEM PHARMACEUTICAL PREPARATION

[75] Inventors: Herman J. Eichel, deceased, late of Columbus, Ohio, by Margaret A. Eichel, executor; Brent D. Massmann, Ballwin, Mo.; Joseph E. Cobb, Jr., Columbus, Ohio

[73] Assignee: Kinaform Technology, Inc., Dayton, Ohio

[*] Notice: The term of this patent shall not extend beyond the expiration date of Pat. No. 5,376,384.

[21] Appl. No.: 354,378

[22] Filed: Dec. 12, 1994

Related U.S. Application Data

[63] Continuation-in-part of Ser. No. 996,097, Dec. 23, 1992, Pat. No. 5,376,384.

[51] Int. Cl.$^6$ ........................................ A61K 9/36
[52] U.S. Cl. ........................ 424/480; 424/469; 424/489; 424/409; 424/472
[58] Field of Search .................... 424/480, 489, 424/472, 473, 409

[56] References Cited

U.S. PATENT DOCUMENTS

| | | | |
|---|---|---|---|
| 3,155,590 | 11/1964 | Miller et al. | 424/468 |
| 3,341,416 | 9/1967 | Anderson et al. | 424/461 |
| 3,488,418 | 1/1970 | Holliday et al. | 424/472 |
| 3,492,397 | 1/1970 | Peters et al. | 424/489 |
| 3,531,418 | 9/1970 | Fanger et al. | 424/490 |
| 4,205,060 | 5/1980 | Monsimer et al. | 424/495 |
| 4,524,060 | 6/1985 | Mughal et al. | 424/459 |
| 4,752,470 | 6/1988 | Mehta | 424/458 |
| 4,772,475 | 9/1988 | Fukui et al. | 424/468 |
| 4,892,740 | 1/1990 | Takasima et al. | 424/474 |
| 4,900,558 | 2/1990 | Barry et al. | 424/461 |
| 4,968,509 | 11/1990 | Radelbaugh et al. | 424/470 |
| 4,983,401 | 1/1991 | Eichel et al. | 424/473 |
| 5,026,559 | 6/1991 | Eichel et al. | 424/458 |
| 5,112,621 | 5/1992 | Stevens et al. | 424/497 |
| 5,133,974 | 7/1992 | Paradissis et al. | 424/480 |
| 5,188,836 | 2/1993 | Muhammed et al. | 424/439 |
| 5,202,128 | 4/1993 | Morella et al. | 424/469 |
| 5,213,808 | 5/1993 | Bar-Shalom et al. | 424/473 |
| 5,320,853 | 6/1994 | Noda et al. | 424/472 |
| 5,376,384 | 12/1994 | Eichel et al. | 424/489 |

FOREIGN PATENT DOCUMENTS

| | | |
|---|---|---|
| 77956 | 5/1983 | European Pat. Off. . |
| 193164 | 9/1986 | European Pat. Off. . |
| 202051 | 11/1986 | European Pat. Off. . |
| 212745 | 4/1987 | European Pat. Off. . |
| 284039 | 9/1988 | European Pat. Off. . |
| 322277 | 6/1989 | European Pat. Off. . |
| 391518 | 10/1990 | European Pat. Off. . |
| 9220326 | 11/1992 | European Pat. Off. . |
| 11687 | 3/1981 | Japan . |
| 12614 | 3/1981 | Japan . |

OTHER PUBLICATIONS

Ozturk et al, "Mechanism of Release from Pellets coated with an Ethylcelloulose-Base Film," *J. of Controlled Release*, vol. 14, No. 3, Dec. 1990.

*Primary Examiner*—Thurman K. Page
*Assistant Examiner*—William E. Benston, Jr.
*Attorney, Agent, or Firm*—Killworth, Gottman, Hagan & Schaeff

[57] ABSTRACT

A delayed, sustained-release pharmaceutical preparation is provided in which a water-soluble drug core is surrounded by a hydratable diffusion barrier which delays drug release for about 2–10 hours. The hydratable diffusion barrier comprises a film-forming polymer such as an acrylic resin, esterified acrylic resin, or ethyl cellulose or mixtures thereof and an additive which controls the rate of hydration and permeability of the hydratable diffusion barrier selected from the group consisting of lubricants, anionic surfactants, plasticizers, inert water-soluble materials, and mixtures thereof. In the preferred sustained-release pharmaceutical preparation, the film-forming polymer is combined with the additive and coated onto core drug granules to produce a diffusion barrier surrounding the core drug and form microparticles when the drug core is the preferred diltiazem hydrochloride, different coating thicknesses of the diffusion barrier are used to provide a long delay component and a short delay component.

17 Claims, No Drawings

DELAYED, SUSTAINED-RELEASE DILTIAZEM PHARMACEUTICAL PREPARATION

CROSS-REFERENCE TO RELATED APPLICATION

This is a continuation-in-part of application Ser. No. 07/996,097, filed Dec. 23, 1992 now U.S. Pat. No. 5,376,384, issued Dec. 27, 1994.

BACKGROUND OF THE INVENTION

The present invention relates to delayed, sustained-release pharmaceutical preparations, and more particularly, to microparticles or tablets formed of a diltiazem core drug coated with a single, hydratable diffusion barrier which allows a prolonged delayed and sustained release drug delivery.

As is well known, the maximum time of effectiveness in many pharmaceutical preparations, particularly those containing a drug such as aspirin, acetaminophen, indomethacin, propranolol hydrochloride, dextromethorphan, diltiazem etc. is only a few hours because of biological modification and/or elimination of the medication in the body. Consequently, repeated doses must be taken at frequent intervals to obtain long term therapeutic levels of drug. Furthermore, these drugs usually dissolve readily in the digestive juices and the total dosage is immediately fed into the blood stream. After high initial peak concentrations, the level of drug in the blood stream constantly decreases because of the biological elimination, so there is little or no therapeutic effect at the end of the period between doses. As a result, the therapeutic effect fluctuates between doses corresponding to the peaks and valleys in the level of drug in the blood.

Many attempts have been made to develop timed-release pharmaceutical preparations which provide a more constant level of the drug in the blood over several hours.

One common approach is to microencapsulate aspirin, for example, with a capsule wall material which provides a slower dissolution rate than free aspirin. The early work in that regard is represented by U.S. Pat. Nos. 3,155,590; 3,341,416; 3,488,418; and 3,531,418. Those patents, among others, disclose dispersing particles of aspirin in a hot cyclohexane solution containing ethyl cellulose and then introducing a phase-separation inducing agent, such as butyl rubber or polyethylene. Upon cooling, the aspirin particles become coated with ethyl cellulose. The coated particles are then admixed with tableting excipients and formed into dosage-sized tablets. When ingested, the tablets disintegrate rapidly and the individual particles of encapsulated aspirin are dispersed in the stomach. The gastric juices slowly diffuse through the capsule walls, dissolve the aspirin, and the dissolved aspirin slowly diffuses or leaches out through the capsule walls into the body. Although the resultant blood level content is sustained to a measurable extent, the aspirin is diffused into the body rapidly enough so there is an initially high blood level content which decreases quite rapidly within a few hours.

As a result, efforts have been made to adjust the rate of dissolution and, thus, control the timing of sustained drug release. See, for example, Peters, U.S. Pat. No. 3,492,397 where the dissolution rate is said to be controlled by adjusting the wax/ethyl cellulose ratio of the applied spray coating, and Mehta, U.S. Pat. No. 4,752,470 where the controlled release characteristics for indomethacin are varied depending on the ratio of ethyl cellulose to hydroxypropyl cellulose in the coating. See also U.S. Pat. Nos. 4,205,060 and 3,488,418 where it is indicated that the rate of dissolution of various drugs can be controlled by varying the thickness of the coating applied to those drugs.

Another method for providing an encapsulated pharmaceutical composition is discussed in published European patent Application No. 77,956, published May 4, 1983. EPO Publication No. 77,956 discloses the use of microcapsules containing a coated core material such as pharmaceutical compounds and foodstuffs. The coating is applied by dispersing core material into a solution containing ethyl cellulose as the wall-forming material. A phase separation of the ethyl cellulose from the dispersion of core material is carried out by cooling the dispersion. During this cooling, an enteric polymer material is incorporated into the ethyl cellulose coating walls by adding the enteric polymer material with stirring while the ethyl cellulose is still in the "gel" state. The enteric polymer material thus added penetrates and is dispersed into the coating walls. When the microcapsules are administered, the release of the active compound does not generally occur in the stomach. However, the enteric polymer material is easily dissolved in the intestinal tract, thereby making the microcapsules porous. The porosity of the microcapsules promotes the rapid release of the active compound in the intestinal tract.

A similar approach is found in Japanese Patent Publication No. 12614/81, published Mar. 23, 1981. Japanese Publication No. 12614/81 discloses an enteric protective coating composition which will not readily dissolve in acidic gastric juices, but rapidly (within minutes) dissolves at the pH found in the intestines. The enteric coating is an aqueous dispersion of, for example, hydroxy propyl methyl cellulose phthalate, a gelling agent such as diacetin, and hydroxy propyl methyl cellulose. See, also, Japanese Patent Publication No. 11687/81, published Mar. 16, 1981, which uses hydroxy propyl methyl cellulose phthalate as an enteric coating.

The systems described in the EPO and Japanese publications are essentially "delayed" release mechanisms. There is a delay of medicament release in the stomach, but once the coated medicament reaches the intestines, the release of medication is rapid. There is no sustained release of medication in the intestines.

Still other systems for sustained-release pharmaceutical preparations are known. For example, Fukui et al, U.S. Pat. No. 4,772,475, relate to a controlled-release pharmaceutical formulation comprising a granular core mixed with water-insoluble polymers such as acrylic acid polymers and copolymers, and cellulose derivatives which allows gradual release of the drug in the gastrointestinal tract.

Mughal et al, U.S. Pat. No. 4,524,060, relate to a sustained-release pharmaceutical composition comprising a mixture of micronised indoramin, a water-channeling agent such as microcrystalline cellulose, and a wetting agent comprising anionic surfactants. The mixture is coated with an enteric coating such as hydroxypropylmethyl cellulose phthalate, polyvinyl acetate phthalate, cellulose acetate phthalate and acrylic resins, or a sustained-release coating such as natural waxes or mixtures of polymers, such as ethyl cellulose, which is permeable to gastro-intestinal juices.

Barry et al, U.S. Pat. No. 4,900,558 disclose a pharmaceutical formulation providing sustained release over a 12-hour period comprising a drug core containing ibuprofen and microcrystalline cellulose, and a coating covering the core comprising a water-insoluble but water-swellable acrylic polymer and a water-soluble hydroxylated cellulose derivative.

In addition, Published EPO application 212745 discloses sustained-release drug particles containing an ibuprofen drug core, an inner coating of an enteric material such as acrylic polymers and copolymers, and an outer coating such as methacrylic acid polymers and copolymers which are insoluble at any pH and act as a diffusion barrier for the drug.

While the above-mentioned references provide a more constant rate of drug release, in some instances, it is desirable to mix the delayed sustained-release preparation with an immediate release drug to obtain a biphasic drug release profile. For example, Radebaugh et al, U.S. Pat. No. 4,968,509, disclose a sustained-release acetaminophen formulation formed by mixing acetaminophen with hydroxyethyl cellulose and a wicking agent such as microcrystalline cellulose, and then adding a povidone granulating agent. The sustained-release formulation may be part of a multi-layered tablet containing an immediate-release layer acetaminophen to quickly elevate and then maintain the blood levels of acetaminophen.

Reference is also made to Eichel, U.S. Pat. No. 5,026,559, which discloses a delayed and sustained-release pharmaceutical preparation comprising a multi-walled coated drug having an inner wall microencapsular enteric coating, such as polymethacrylic acid/acrylic acid copolymer or cellulose acetate phthalate, a solid acid either incorporated in the enteric layer or layered over the enteric layer, and an outer wall microencapsulated control coating, such as polymethacrylic acid ester copolymer or ethyl cellulose. The solid acid delays drug release by maintaining the enteric polymer in an impermeable state until the acid diffuses out of the drug or is neutralized. The multi-walled coated drug is admixed with an uncoated drug having immediate therapeutic properties upon dissolution in the stomach.

However, many of the multi-walled preparations described above do not provide prolonged delayed release of the drug prior to initiation of sustained release, which is important when biphasic release profiles are desired.

Accordingly, the need exists for a delayed, sustained-release pharmaceutical preparation which provides a longer delay of drug dissolution which would provide greater flexibility in designing sustained-release profiles for a wide variety of drugs, provides constant blood concentration levels, and is simply and economically produced.

SUMMARY OF THE INVENTION

The invention provides a delayed, sustained release of a water soluble drug coated with a hydratable diffusion barrier which delays drug release after ingestion and thereafter provides for sustained release of the drug. Thus, the diffusion barrier of the present invention initially prevents drug release, and then is slowly hydrated to become permeable to dissolved drug and provide a sustained release of the drug.

The length of time for the delay is controlled by the rate of hydration and the thickness of the diffusion barrier. The drug release rate subsequent to the delay is determined by the thickness and permeability of the hydrated diffusion barrier. Thus, it is possible to regulate the rate of hydration and permeability of the diffusion barrier so that the desired delayed, sustained-release drug profiles can be achieved.

The hydratable diffusion barrier preferably comprises film-forming polymers which are insoluble under intestinal conditions and additives which control the rate of hydration and permeability of the diffusion barrier. The preferred insoluble film-forming polymers are aqueous dispersions of fully esterified acrylic resins such as Eudragit NE30D available from Rohm Pharma GmbH of Weiterstadt, Germany, fully esterified acrylic resins containing quaternary amine side chains such as Eudragit RS30D from Rohm Pharma, aqueous dispersions of ethyl cellulose such as Aquacoat ethyl cellulose emulsion, available from FMC Corp. of Chicago, Illinois or Surelease, available from Colorcon of West Point, Pennsylvania or mixtures thereof. Polymers dissolved in organic solvents may also be used.

The additives which control the rate of hydration and permeability of the diffusion barrier are preferably selected from the group consisting of anionic surfactants, lubricants, plasticizers, inert water soluble materials, and mixtures thereof. These additives may include sodium lauryl sulfate, magnesium stearate, citric acid, simethicone, talc, acetyl-tributyl-citrate, and mixtures thereof.

Magnesium stearate decreases the hydration rate, increases the hydrated permeability of the diffusion barrier, and also prevents the drug beads from agglomerating during processing. Preferably, the magnesium stearate is used in an amount of approximately 0 to 50% of the weight of the film-forming polymers.

Anionic surfactants are preferably used in an amount of from approximately 0 to 2% of the film-forming polymer weight, and function to increase both the permeability and hydration rate of the diffusion barrier. Inert, water-soluble materials are preferably used in amounts of approximately 0 to 20% of the film-forming polymer weight, and also increase both the permeability and hydration rate of the diffusion barrier.

Suitable plasticizers include either hydrophilic or hydrophobic plasticizers. Hydrophilic plasticizers increase both the permeability and hydration rate of the diffusion barrier, while hydrophobic plasticizers decrease both the permeability and hydration rate of the diffusion barrier. The plasticizers are preferably used at amounts from approximately 0–30% of the film-forming polymer weight.

The core drug is preferably a water soluble drug having a solubility of greater than approximately 10 grams per liter in intestinal fluid. The core drug may be propranolol hydrochloride, quinidine gluconate, dextromethorphan hydrobromide, diphenhydramine hydrochloride, disopyramide phosphate, verapamil hydrochloride, etc., but the most preferred is diltiazem hydrochloride. The core drug may be in tablet form but preferably is granular so as to form multi-unit microparticles. Thus, the core drug may be coated on sugar spheres, blended with wax incipients, or otherwise formulated to produce core drug granules. Preferably, the core drug granules are spherical microparticles having a size range from about 500 to 1500 microns.

The hydratable diffusion barrier is formed by combining aqueous dispersions of the film-forming polymer and additive (which controls the rate of hydration and permeability of the diffusion barrier), and then coating the mixture onto core drug granules by a spray coating process, resulting in a hydratable diffusion barrier.

When diltiazem hydrochloride is the core drug, as preferred, it is desirable to combine two batches into a dosage form. One batch, the long delay batch, has in it core drug coated with a hydratable diffusion barrier layer which is at and about 20% (by weight) of the coated bead. That diffusion barrier effectively controls release of the drug so that less than about 5% of the drug dissolves within 9 hours in a U.S.P. basket dissolution at 100 rpm in 1 liter of 0.05 M pH 6.8 phosphate buffer and so that release of therapeutic levels of the drug occurs from the 12th hour to the 24th hour.

The other batch, the short delay batch, has in it core drug coated with a hydratable diffusion barrier layer which is not as thick as that used in the long delay batch (i.e. about 11–18% (by weight) of the coated bead). That diffusion barrier effectively controls release of the drug so that less than about 10% of the drug dissolves within 2 hours in a U.S.P. basket dissolution at 100 rpm in 1 liter of 0.05 M pH 6.8 phosphate buffer but is rapidly hydrated within 2–12 hours after ingestion whereby over 90% of the drug is released within 12 hours.

Accordingly, it is an object of the present invention to provide a delayed, sustained-release pharmaceutical preparation having a single, hydratable diffusion barrier coated on a core drug which allows prolonged delayed and sustained-release drug delivery. It is also an object of the present invention to control the coat rate and formulation of the aqueous dispersions of film-forming polymer and additive in different batches to provide hydratable diffusion barriers which result in long delay and short delay release.

These, and other objects and advantages of the present invention will become apparent from the following detailed description, and the appended claims.

DETAILED DESCRIPTION OF THE PREFERRED EMBODIMENTS

The preferred delayed, sustained-release pharmaceutical preparation of the present invention is a water soluble core drug surrounded by a hydratable diffusion barrier comprising an insoluble film-forming polymer such as Eudragit NE30D (Rohm Pharma), Eudragit RS30D (Rohm Pharma), Aquacoat (FMC Corp.) ethyl cellulose, or mixtures thereof and an additive which controls the rate of hydration and permeability of the diffusion barrier, together in microparticle form.

The core drug is preferably a soluble orally administered drug. The solubility of the drug in the intestines should be greater than 10 grams per liter as drugs with lower solubility will not dissolve and diffuse through the hydrated diffusion barrier at adequate rates. Examples of suitable drugs include propranolol hydrochloride, quinidine gluconate, dextromethorphan hydrobromide, diphenhydramine hydrochloride, disopyramide phosphate, and verapamil hydrochloride. Most preferred is diltiazem hydrochloride.

The hydratable diffusion barrier is formed by combining the film-forming polymer dispersion and an additive dispersion, and then spray coating the core drug.

In one embodiment, the additive dispersion comprises from about 5 to 20% magnesium stearate, from about 75 to 95% water, and from about 0 to 5% citric acid.

In another embodiment, the additive dispersion comprises from about 5 to 20% magnesium stearate, from about 80 to 95% water, and 0 to 1% simethicone emulsion.

In yet another embodiment, the additive dispersion comprises 3–10% acetyltributyl citrate (ATBC), 7–20% talc and 70–90% water.

The preferred process for applying the hydratable diffusion barrier to the core drug is a fluid bed spray coating process such as the Wurster process or the tangential spray rotor process. Other spray coating processes such as pan coating or the immersion tube process may be used. The additive comprises 5–40% (solids basis) of the combined aqueous dispersions of additive dispersion and film-forming polymer dispersion. The drug beads are coated with the dispersion and tray dried at 35° C. to 60° C. for 8 hours to 5 days (120 hours).

To obtain delays of 9 hours or longer, as is found in a long delay batch of diltiazem, the diffusion barrier should be at least 20% (by weight) of the coated bead and is preferably 22–26% (by weight) of the coated bead. The upper limit of the diffusion barrier thickness is determined by the potency requirements for the long delay batch to obtain delays of about 2 hours, for the short delay batch the coating is thinner (i.e. 11–18% (by weight) of the coated bead and preferably 13–16% (by weight) of the coated bead). In each instance, the permeability of the hydrated diffusion barrier should be designed to provide the desired release rate of the drug after the delay has elapsed.

In order that the invention may be more readily understood, reference is made to the following examples, which are intended to illustrate the invention, but are not to be taken as limiting the scope thereof.

EXAMPLE I

60% active propranolol hydrochloride beads were prepared by coating a solution of propranolol hydrochloride in water onto 25–30 mesh sugar spheres. A diffusion barrier coating formulation was prepared by combining 67.6 parts by weight Eudragit NE30D from Rohm Pharma with 0.1 part by weight sodium lauryl sulfate. 3.6 parts by weight magnesium stearate was dispersed into 25.1 parts by weight water and added to the Eudragit NE30D and sodium lauryl sulfate. 3.6 parts by weight Eudragit RS30D from Rohm Pharma was then added with stirring. In a fluidized bed with a Wurster insert 425 grams of the 60% propranolol beads were coated with the coating formulation using a spray rate of 7 grams per minute and an inlet temperature of 30° C. Samples were taken after spraying 425 grams (20% coat), 507 grams (25% coat) and 729 grams (30% coat). The coated beads were tray dried at 40° C for 18 hours. The dissolutions were performed by the U.S.P. basket dissolution method at 100 rpm in 1 liter of 0.05 M pH 6.8 phosphate buffer. The results of a dissolution study are set forth in Table 1 below.

TABLE I

| Propranolol Hydrochloride Dissolution | | | |
| --- | --- | --- | --- |
| | Percent Dissolved | | |
| Time (hrs) | 20% coat | 25% coat | 30% coat |
| 2 | 1% | 0% | 0% |
| 4 | 3% | 2% | 0% |
| 5 | 7% | 2% | 0% |
| 6 | 16% | 3% | 0% |
| 7 | 32% | 6% | 0% |
| 8 | 53% | 13% | 1% |
| 10 | 83% | 36% | 3% |
| 12 | 93% | 67% | 13% |
| 13 | 98% | 79% | 21% |

EXAMPLE II

50% active diltiazem hydrochloride beads were prepared by coating a solution of 27.3 parts by weight diltiazem, 0.5 parts hydroxy propyl methyl cellulose, 0.8 parts microcrystalline cellulose, and 1.4 parts magnesium stearate in 70 parts water. 425 grams of the 50% active diltiazem beads were coated with the coating formulation described in Example 1 by the Wurster process. Samples were taken after spraying 189 grams (10% coat), 277 grams (14% coat) and 373 grams (18% coat). The coated beads were tray dried at 40° C for 18 hours. The dissolutions were performed as in Example I and the results are set forth in Table II below.

TABLE II

Diltiazem Hydrochloride Dissolution

| Time (hrs) | Percent Dissolved | | |
|---|---|---|---|
| | 10% coat | 14% coat | 18% coat |
| 2 | 3% | 3% | 2% |
| 4 | 16% | 4% | 2% |
| 6 | 44% | 15% | 3% |
| 8 | 73% | 38% | 11% |
| 10 | 85% | 59% | 28% |
| 14 | 96% | 82% | 59% |
| 18 | 100% | 93% | 77% |

EXAMPLE III

53% active diltiazem HCl beads were prepared by coating 25–30 mesh sugar spheres with a solution of 27.8 parts diltiazem HCl in 70 parts water containing 2.2 parts microcrystalline cellulose. A coating formulation was prepared by dispersing 10.8 parts magnesium stearate in 17.2 parts water containing 0.2 parts citric acid and adding to 64.6 parts Eudragit NE30D from Rohm Pharma and 7.2 parts Aquacoat from FMC. 318 grams of this coating formulation was coated onto 450 grams of the 53% active diltiazem HCl beads using the Wurster process spraying at 5.5 grams per minute with an inlet temperature of 30° C. The coated beads were dried 18 hours at 40° C. The dissolution was performed as in Example I and the results are set forth in Table III below.

TABLE III

Diltiazem Hydrochloride Dissolution

| Time (hrs) | Percent Dissolved 15% Coat |
|---|---|
| 2 | 2% |
| 4 | 5% |
| 6 | 34% |
| 8 | 59% |
| 10 | 73% |
| 14 | 81% |
| 18 | 89% |

EXAMPLE IV

65% active disopyramide phosphate beads were prepared by coating a solution of 50 parts disopyramide phosphate, 2.5 parts Povidone K30, a binder available from GAF of Texas City, Texas, 0.2 parts talc, and 47.3 parts water onto 25–30 mesh sugar spheres using the Wurster process. A coating formulation was prepared by dispersing 3.3 parts magnesium stearate in 31 parts water containing 0.1 part simethicone emulsion USP and adding it to 65.6 parts Eudragit NE30D from Rohm Pharma. The coating formulation was applied to 3500 grams of the 65% active disopyramide phosphate beads by the Wurster process using a spray rate of 40 grams per minute and an inlet air temperature of 40° C. Samples were taken after spraying 3454 grams (18.5% coat), 4292 grams (22% coat), and 5918 grams (28% coat). Dissolutions were performed as in Example I and are set forth in Table IV-A below.

TABLE IV-A

Disopyramide Phosphate Dissolution

| Time (hrs) | Percent Dissolved | | |
|---|---|---|---|
| | 18.5% coat | 22% coat | 28% coat |
| 1 | 1% | 0% | 0% |
| 2 | 2% | 0% | 0% |
| 3 | 5% | 0% | 0% |
| 5 | 13% | 4% | 2% |
| 8 | 29% | 14% | 8% |
| 12 | 65% | 50% | 29% |
| 16 | 87% | 81% | 49% |
| 20 | 100% | 96% | 68% |
| 24 | 100% | 99% | 85% |

The disopyramide phosphate beads with the 28% coat were tested in healthy human subjects to determine the concentration of drug in plasma versus time after dosing. A single dose containing 300 mg of disopyramide was administered to four subjects. Blood samples were taken over a 24 hour period and the plasma concentration of disopyramide was determined. The results presented in Table IV-B show that the delayed then sustained release profile occurs in human subjects as well as during in vitro dissolution testing. Drug is not detected in the plasma until 4 hours after dosing. The drug plasma concentration then increases to a plateau which is maintained from 18 to 24 hours.

TABLE IV-B

Disopyramide Phosphate Biostudy
300 mg dose, 28% coated beads

| Time After dose (hrs) | Plasma Disopyramide mg/L |
|---|---|
| 2 | 0 |
| 4 | 0.09 |
| 8 | 0.39 |
| 12 | 0.65 |
| 16 | 1.07 |
| 18 | 1.16 |
| 22 | 1.16 |
| 24 | 1.18 |

EXAMPLE V

This example illustrates the concentric coating of a fast release component onto the delayed sustained-release disopyramide phosphate of Example IV. 500 grams of the 28% coated beads from Example IV were coated with 130 grams of a coating formula composed of 47.5 parts disopyramide phosphate, 2.5 parts talc, 2.5 parts Povidone K30 from GAF, and 47.5 parts water using the Wurster process with a spray rate of 4.5 grams per minute and an inlet temperature of 50° C. These beads were then coated with 118 grams of a coating formula composed of 57 parts Eudragit NE30D from Rohm Pharma, 3 parts magnesium stearate, and 40 parts water. The dissolution procedure described in Example I resulted in the release rate profile shown in Table V. The concentrically coated fast release component provides drug release for the first 4 hours then release from the second slow release component initiates at about 7 hours.

TABLE V

Disopyramide Biphasic Release

| Time (hrs) | Percent Dissolved Disopyramide mg/L |
|---|---|
| 1 | 5% |
| 2 | 10% |
| 4 | 18% |
| 8 | 27% |
| 12 | 42% |
| 16 | 61% |
| 20 | 75% |
| 24 | 87% |

EXAMPLE VI

This example illustrates combining a short delay batch (Batch A) with a long delay batch (Batch B). 54% active diltiazem hydrochloride beads were prepared by coating a solution 25 parts diltiazem hydrochloride, 5 parts polyvinyl povidone, 5 parts magnesium stearate, and 65 parts water onto 35–45 mesh sugar spheres using the Wurster process. A coating formulation was prepared by mixing for 60 minutes 47.9 parts Eudragit RS30D suspension (Rohm Pharma) with 2.9 parts of acetyltributyl citrate (ATBC) sold under the trademark Citroflex A-4 (from Morflex, Inc, Greensboro, N.C.) and then adding 5.8 parts talc and 43.4 parts water. 5,890 g of the 54% active seeds were coated with 3,826 g of the coating formulation by the Wurster process with an average spray rate of 54 g/min and with a product temperature maintained from 26°–31° C. A 48.9 g sample was dusted with 0.49 g of talc and cured for 72 hours at 55° C. The dissolution of Batch A was performed as in Example I and the results are set forth in Table VI-A below:

TABLE VI-A

Batch A Diltiazem Hydrochloride Dissolution

| Time (hrs) | % Dissolved |
|---|---|
| 1 | 4% |
| 2 | 7% |
| 4 | 41% |
| 6 | 81% |
| 9 | 88% |
| 12 | 92% |
| 15 | 96% |
| 18 | 97% |

As can be seen the Batch A pharmaceutical preparation releases drug from the 2nd and 9th hour of the dissolution test (fast component). With Batch B, 57% active diltiazem beads were prepared in the same manner as the drug beads in Batch A. A coating formulation was prepared as in Batch A. 6,405 g of 57% active beads were coated with 8,318 g of coating formula using the Wurster process with an average spray rate of 59 g/min and maintaining the product bed temperature at 26°–31° C. A 108.1 g sample was dusted with 1.1 g of talc and cured at 55° C. A dissolution of Batch B was performed as in Example I and the results are set forth in Table VI-B below.

TABLE VI-B

Batch B Diltiazem Hydrochloride Dissolution

| Time (hrs) | % Dissolved |
|---|---|
| 1 | 2% |
| 2 | 2% |
| 4 | 2% |
| 6 | 5% |
| 9 | 5% |
| 12 | 14% |
| 15 | 40% |
| 18 | 68% |
| 21 | 83% |
| 24 | 87% |

As can be seen the Batch B pharmaceutical preparation releases the majority of the drug from the 12th hour to the 24th hour of the dissolution test.

A mixture containing 40% of the drug in Batch A beads (fast component and 60% of the drug in Batch B beads (slow component) give a two-tiered release profile as set forth in Table VI-C below:

TABLE VI-C

Diltiazem Hydrochloride Dissolution

| Time (hrs) | % Dissolved |
|---|---|
| 1 | 3% |
| 2 | 4% |
| 4 | 20% |
| 6 | 33% |
| 9 | 37% |
| 12 | 44% |
| 15 | 58% |
| 18 | 74% |
| 21 | 81% |
| 24 | 85% |

What is claimed is:

1. A delayed, sustained-release pharmaceutical preparation comprising:
   a) a core containing diltiazem hydrochloride drug, and
   b) a hydratable diffusion barrier surrounding said core and having a thickness of at least 20 microns, said barrier comprising a film-forming polymer which is insoluble under both stomach and intestinal conditions and a sufficient amount of additive to control the hydration rate and permeability of said hydratable diffusion barrier so that less than 5% of said drug dissolves within 2 hours in a U.S.P. basket dissolution at 100 rpm in 1 liter of 0.05M pH 6.8 phosphate buffer but so that said hydratable diffusion barrier is slowly hydrated to become permeable to dissolved drug within 2 to 12 hours after ingestion;
   whereby said hydratable diffusion barrier delays release of therapeutic levels of said drug for about 2–12 hours after ingestion, and thereafter provides for sustained-release of therapeutic levels of said drug.

2. The delayed, sustained-release pharmaceutical preparation of claim 1 wherein said film-forming polymer is selected from the group consisting of a fully esterified acrylic resin and a fully esterified acrylic resin having quaternary amine side chains.

3. The delayed, sustained release pharmaceutical preparation of claim 1 wherein said film-forming polymer and said additive are applied to said core drug as aqueous dispersions.

4. The delayed, sustained-release pharmaceutical preparation of claim 3 wherein said additive dispersion comprises from about 3–10% acetyltributyl citrate, 7–20% talc and 70–90% water.

5. The delayed, sustained release pharmaceutical preparation of claim 4 wherein said film-forming polymer dispersion comprises a mixture of water and a fully esterified acrylic resin containing quaternary amine side chains.

6. The delayed, sustained-release pharmaceutical preparation of claim 5 wherein said additive comprises from about 5 to 40% (solids basis) of the total of said additive dispersion and said film-forming polymer dispersion.

7. The delayed, sustained-release pharmaceutical preparation of claim 1, wherein said aqueous dispersions have been dried at 35°–60° C. for 8–120 hours to form said hydratable diffusion barrier.

8. The delayed, sustained-release pharmaceutical preparation of claim 1 wherein the thickness of said hydratable diffusion barrier is about 30 to 200 microns.

9. The delayed, sustained-release pharmaceutical preparation of claim 8 wherein said core drug is in the form of particles from about 500–1500 microns in diameter.

10. A delayed, sustained-release pharmaceutical preparation comprising a mixture of a long delay component and a short delay component, wherein
  i) said long delay component comprises:
    a) a core containing diltiazem hydrochloride drug, and
    b) a hydratable diffusion barrier surrounding said core and having a thickness of at least 20 microns, said barrier comprising a film-forming polymer which is insoluble under both stomach and intestinal conditions and a sufficient amount of additive to control the hydration rate and permeability of said hydratable diffusion barrier so that less than 5% of said drug dissolves within 2 hours in a U.S.P. basket dissolution at 100 rpm in 1 liter of 0.05M pH 6.8 phosphate buffer but so that said hydratable diffusion barrier is slowly hydrated to become permeable to dissolved drug within 2 to 12 hours after ingestion;
    whereby said hydratable diffusion barrier delays release of therapeutic levels of said drug for about 2–12 hours after ingestion, and thereafter provides for sustained-release of therapeutic levels of said drug from the 12th hour to the 24th hour, and
  ii) said short delay component comprises:
    a) a core containing diltiazem hydrochloride drug, and
    b) a hydratable diffusion barrier surrounding said core, said barrier comprising a film-forming polymer which is insoluble under both stomach and intestinal conditions and a sufficient amount of additive to control the hydrate rate and permeability of said hydratable diffusion barrier so that less than 10% of said drug dissolves within 2 hours in a U.S.P. basket dissolution at 100 rpm in 1 liter of 0.05M pH 6.8 phosphate buffer but so that said hydratable diffusion barrier is rapidly hydrated within 2–12 hours after ingestion to become permeable to dissolved drug whereby over 90% of said drug is released within 12 hours.

11. The delayed, sustained release pharmaceutical preparation of claim 10 wherein said film-forming polymer is selected from the group consisting of a fully esterified acrylic resin and a fully esterified acrylic resin having quaternary amine side chains.

12. The delayed, sustained-release pharmaceutical preparation of claim 10 wherein said film-forming polymer and said additive are applied to said core drug as aqueous dispersions.

13. The delayed, sustained-release pharmaceutical preparation of claim 12 wherein said additive dispersion comprises from about 3–10% acetyltributyl citrate, 7–20% talc and 70–90% water.

14. The delayed, sustained release pharmaceutical preparation of claim 13 wherein said film-forming polymer dispersion comprises a mixture of water and a fully esterified acrylic resin containing quartenary amine side chains.

15. The delayed, sustained-release pharmaceutical preparation of claim 14 wherein said additive comprises from about 5 to 40% (solids basis) of the total of said additive dispersion and said film-forming polymer dispersion.

16. The delayed, sustained-release pharmaceutical preparation of claim 15 wherein said diffusion barrier comprises at least 20% by weight of said long delay component.

17. The delayed, sustained-release pharmaceutical preparation of claim 16 wherein in said diffusion barrier comprises 11–18% by weight of said short delay component.

\* \* \* \* \*